United States Patent [19]

Fasline et al.

[11] Patent Number: 4,732,146
[45] Date of Patent: Mar. 22, 1988

[54] WOUND DRESSING RETENTION APPARATUS

[76] Inventors: Ronald J. Fasline, 2110 Arms Dr., Girard, Ohio 44420; Randall J. Hartwig, 4133 Euclid Blvd., Youngstown, Ohio 44512

[21] Appl. No.: 85,191

[22] Filed: Aug. 14, 1987

[51] Int. Cl.⁴ ............................................. A61F 13/00
[52] U.S. Cl. ..................................................... 128/155
[58] Field of Search ............................... 128/155, 156

[56] References Cited

U.S. PATENT DOCUMENTS

| | | | |
|---|---|---|---|
| 3,297,028 | 1/1967 | Murray | 128/157 |
| 3,417,749 | 12/1968 | Bailey | 128/171 |
| 3,561,440 | 2/1971 | Bayer | 128/132 |
| 3,779,242 | 12/1973 | McCullough | 128/171 |
| 4,181,127 | 1/1980 | Linsky | 128/155 |
| 4,221,215 | 9/1980 | Mandelbaum | 128/155 |
| 4,263,906 | 4/1981 | Finley | 128/157 |
| 4,531,521 | 7/1985 | Haverstock | 128/335 |
| 4,556,055 | 12/1985 | Bonner, Jr. | 128/155 |

OTHER PUBLICATIONS

Advertisement Brochure for TEGRADERM® Transparent Dressing, by Medical Products Division/3M, 225-55, 3M Center, St. Paul, MN 55144.

Primary Examiner—Gregory E. McNeill
Attorney, Agent, or Firm—Renner, Kenner, Greive, Bobak & Taylor

[57] ABSTRACT

An apparatus for retaining wound dressing to a wound on a patient's body. The apparatus includes a resilient framework (11) positionable proximate to the wound. The framework (11) has a body engaging surface (25) for selective engagment with the patient's body and a top surface (20) opposite the body engaging surface (20). The framework (11) presents a dressing receiving opening (12) continually accessible from the top surface (20) when the body engaging surface (25) is engaged with the patient's body. Straps (13) are provided for retaining the wound dressing (15) by bridging a portion of the dressing receiving opening (12). Releasable fasteners (23, 24) removably secure the straps (13) to a portion of the framework (11).

15 Claims, 6 Drawing Figures

WOUND DRESSING RETENTION APPARATUS

TECHNICAL FIELD

The present invention relates generally to wound dressings. More specifically, the present invention relates to a surgical wound dressing which provides a controlled tension to a wound. More particularly, the present invention relates to a surgical wound dressing retention apparatus for securing dressing to a wound while providing limited access to the wound for tubing, leads or other instruments. Specifically, the present invention pertains to a surgical wound dressing retention apparatus which permits replacement of the wound dressing, and medical attendance to the wound, without traumatizing the skin tissue surrounding the wound.

BACKGROUND ART

Post operative care of a patient involves constant attention to the surgical incision. Such attention necessitates cleaning of the wound and replacement of the dressing so as to facilitate healing and to avoid infection of the wound. While such constant and repetitive attention is intended to aid the healing process, the procedures used may actually agravate the wound and therefore result in a longer period of recovery.

In its most rudimentary form, surgical wound dressing involves the application of sterile gauze or similar bandage secured in place on the wound using adhesive tape. A variation of this practice involves the use of gauze pads having adhesive strips thereon which then retain the pads onto the wound.

In each of these practices, the adhesive tape or strip must be removed from the patient's skin whenever the dressing is changed. As a result, the skin soon becomes irritated and inflamed. Furthermore, whenever the adhesive tape or strip is pulled off the skin, it is likely to pull at the wound and any suture closing the incision, thereby reopening portions of the wound and retarding the healing process.

Various efforts have been undertaken to provide wound dressing which are less likely to agravate the wound or the surrounding skin. These generally involve a pair of adhesive members secured to opposite sides of the incision with either cords, elastic bands, or adhesive strips bridging the wound so as to draw the incision closed and/or to hold a dressing material onto the wound. Nevertheless, when the dressing material is being changed, the tension on the wound is released causing a portion of the healing wound to reopen, again prolonging the recovery process.

Another wound bandage concept involves suturing a flexible frame member to the body about the wound. A replaceable wound dressing, also having a flexible frame member is removably affixed to the first frame member. Thus, when a change of wound dressing is required, the replaceable wound dressing with the second frame member is discarded and replaced with a clean wound dressing having a second frame member. Such a wound dressing totally encompasses the wound making it very difficult to route drainage and/or irrigation tubs, and the like, from the affected region.

Despite the various attempts to provide a wound dressing which permits attendance to the wound, including cleaning of the wound and replacement of the dressing, none allows for such attendance without causing undue aggravation to the wound proper and/or the surrounding skin. Additionally, no known wound dressing enables the use of commonly available dressing material in amounts required; nor do they permit access for the routing of drainage and/or irrigation tubes and the like.

DISCLOSURE OF THE INVENTION

It is, therefore, a primary object of the present invention to provide a surgical wound dressing apparatus capable of permitting attendance to the wound without aggravating the wound or the surrounding skin.

It is another object of the present invention to provide a surgical wound dressing apparatus, as above, which permits the usage of common dressing material in amounts necessary to meet the varying requirements during the healing process.

It is a further object of the present invention to provide a surgical wound dressing apparatus, as above, which permits limited access to the bandaged wound for the convenient routing of drainage and/or irrigation tubes and the like.

It is still another object of the present invention to provide a surgical wound dressing apparatus, as above, which provides means for retaining drainage and/or irrigation tubes and the like in relationship to the wound.

These and other objects of the present invention, as well as the advantages thereof over existing and prior art forms, which will be apparent in view of the following specification, are accomplished by means hereinafter described and claimed.

In general, an apparatus for retaining wound dressing to a wound on a patient's body, according to the concept of the present invention includes a resilient frame positionable proximate to the wound. The frame has a body engaging surface for selective engagement with the patient's body and a top surface opposite the body engaging surface. The frame presents a dressing receiving region continually accessible from the top surface when the body engaging surface is engaged with the patient's body. Straps are provided for retaining the wound dressing by bridging a portion of the dressing receiving region. Releasable fasteners secure the straps to a portion of the frame means.

EXEMPLARY EMBODIMENTS FOR CARRYING OUT THE INVENTION

Figure 1:
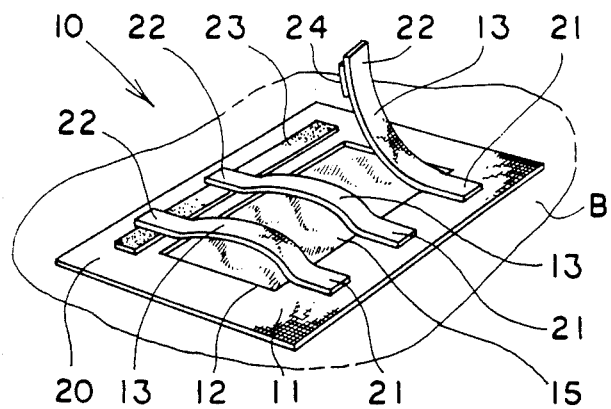
FIG. 1 is a perspective view of a surgical wound dressing retention apparatus embodying the concept of the present invention.

A surgical wound dressing retention apparatus according to the concept of the present invention is indicated generally by the numeral 10 in FIG. 1 of the attached drawings. The surgical wound dressing retention apparatus 10 is depicted in FIGS. 1 and 2 environmentally with a patient's body B, represented in broken lines.

The retention apparatus includes a framework 11 which preferably is a thin pliable member that readily may conform to the contours of a patient's body. Any number of different materials may be used to construct framework 11, provided they possess the desirable characteristics of being moisture vapor permeable and hypoallergenic so as to permit the patient's skin to breath and to reduce skin maceration.

Figure 2:
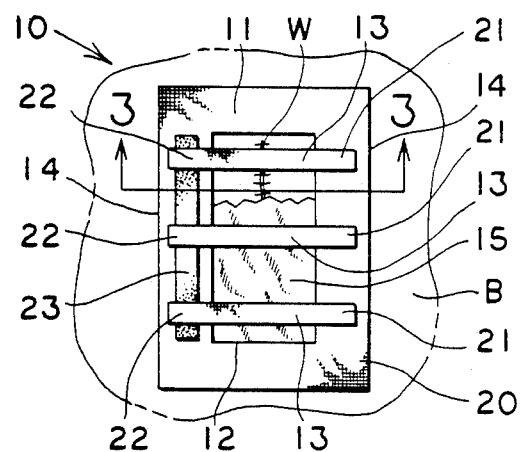
FIG. 2 is a top plan view of the surgical wound dressing retention apparatus depicted in FIG. 1.

As depicted in FIG. 2, framework 11 may be substantially rectangular in shape with a centrally located opening 12 therein. One or more straps 13 extend between two opposite legs 14 of framework 11, bridging opening 12. Straps 13 likewise are constructed of thin pliable material. It also may be desirable for straps 13 to be constructed of an elastic material so as to be capable of generating slight retention pressure on dressing material 15, as will be appreciated hereinbelow.

Straps 13 are so affixed to the top surface 20 of framework 11 to permit total or partial removal of straps 13, thereby providing access to opening 12 and dressing material 15. If straps 15 are partially removable, they may be permanently fixed at one end 21 to one leg 14 of framework 11, as by sewing, adhesive or otherwise bonding end 21 to leg 14. The other end 22 of strap 13 is removably securable to the opposite leg 14 of framework 11 using a suitable, releasable fastener. Any number of releasable fasteners may be employed to removably secure end 22 to leg 14, including snaps, buttons or releasable adhesives; however, it has been found to be most desirable to use a suitable hook and loop fastener, such as VELCRO hook and loop fasteners (VELCRO is a registered trademark of Velcro, Inc.) When using a hook and loop fastener system, a strip of loop material 23 may be secured to leg 14 of framework 11, while end 22 of each strap 13 carries a corresponding pad of hook material 24. As depicted in FIG. 2, loop strip 23 may extend substantially the full length of opening 12, the full perimeter of opening 12 or at selected region about opening 12. Straps 13, with hook pads 24, then can be secured at any location along loop strip 23, in either a parallel or unparallel configuration, or if desired in a criss-cross configuration, to meet the specific needs of the user.

While the foregoing discussion has described straps 13 as being permanently fixed at one end 21 to framework 11, it should be appreciated that such end 21 also could be removably affixed in the same manner as end 22. In such fashion, straps 13 may be completely removable from framework 11, thereby allowing greater latitude in selecting the number and orientation of straps 13 needed to hold securely dressing material 15.

Figure 3:
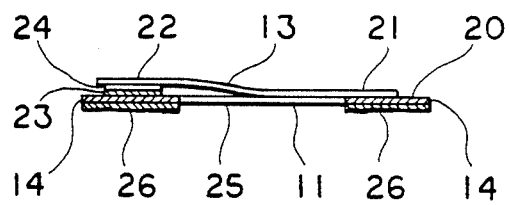
FIG. 3 is a cross-section of the surgical wound dressing retention apparatus taken substantially along line 3—3 of FIG. 2.

The surgical wound dressing retention apparatus 10 preferably is adhesively secured to a patient's body. With reference to FIG. 3 securement can be effected by coating the body engaging surface 25 of framework 11 with a suitable, pressure sensitive adhesive 26. As it is intended that the retention apparatus 10 remain secured to the patient for an extended period of time, adhesive 26 should be a hypoallergenic, moisture resistant type. Many different adhesives meeting these cirteria are presently available in the medical/pharmaceutical industry and may, therefore, be used in conjunction with the present invention.

Preferably, the adhesive 26 may be applied onto framework 11 during fabrication of the retention apparatus 10 and provided with a suitable protective covering. In use, the covering can be removed and the retention apparatus 10 can be applied to the patient's body B, as depicted in FIGS. 1 and 2.

Alternatively to adhesive 26, the retention apparatus 10 may be secured using suitable medical adhesive tape. Strips of tape may be applied along the peripheral edge of framework 11 so as to retain it in position relative to the wound.

The unique structural features of the surgical wound dressing retention apparatus 10 may be more fully understood and appreciated by considering the same in use. For this purpose, reference is made to FIGS. 1 and 2, which depict the retention apparatus 10 as used in the environment of a patient's body B; FIG. 2 depicts a portion of dressing material removed so as to expose a portion of a wound W for ease of discussion.

After the wound W has been suitably prepared for bandaging—that is, suturing, if needed, is completed, and the wound W has been cleaned—the retention apparatus 10 is positioned onto the patient's body B. Specifically, framework 11 is aligned such that the wound W is located substantially centrally within opening 12. Body engaging surface 25 is presented onto the patient's skin surrounding the wound W, and held thereto with adhesive 26.

Once framework 11 is adhered to the patient's body B, straps 13 are removed from opening 12, thereby exposing the wound W. Suitable dressing material 15 is presented onto the wound W via opening 12. Depending upon the size and nature of the wound W and the stage of the recovery process, dressing material 15 may be any one or more of a variety of materials, including cotton, gauze, surgical packing, or the like. When the desired amount of dressing material 15 is applied to the wound W, staps 13 are bridged across opening 12 and releasably secured to framework 11, as hereinabove discussed, thereby retaining dressing material 15 on the wound W. Thereafter, whenever it is necessary to change the wound dressing, or otherwise attend to the wound W, straps 13 need only be undone and dressing material 15 removed and replaced. Framework 11 remains attached to the patient's skin throughout successive replacements of wound dressing 15.

It should be appreciated that the surgical wound dressing 10 heretofore described, is usable with many different types of wound dressing involving different types of wounds at various stages of recovery. Indeed, in large deep wounds, wherein the outer layers of tissue and muscle remain open while the interior tissue heals, the wound can be packed with suitable packing held in place with the present invention. Subsequently, when the wound heals sufficiently, the wound packing can be replaced with a topical dressing covering the surface of the wound during completion of the healing process.

While the foregoing embodiment has proven to be adaptable to a variety of wound applications, the advantages and characteristics associated therewith are likewise associated with alternative embodiments, thereby extending the utility of the present invention to a greater number of situations.

Figure 4:
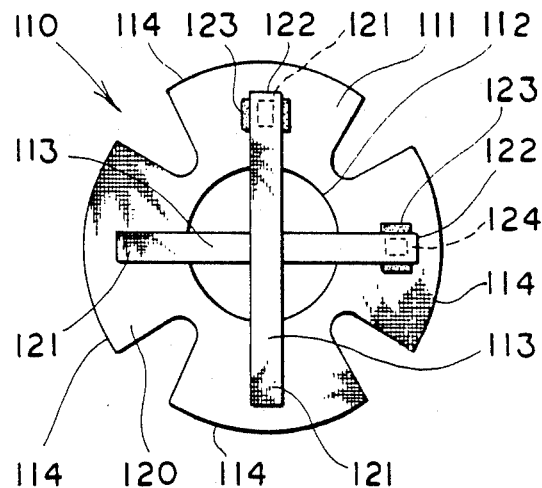
FIG. 4 is an alternative configuration for a surgical wound dressing retention apparatus embodying the concept of the present invention.

With reference to FIG. 4, an alternative embodiment of a surgical wound dressing retention apparatus is indicated generally by the numeral 110. The embodiment employs a substantially annular, cloverleaf-shaped, framework 111 with a centrally located cylindrical opening 112. A pair of flexible straps 113 bridge opening 112 in a criss-cross fashion to retain wound dressing within opening 112. A plurality of lobes 114 extend radially outward about framework 111 so as to present a larger, more flexible surface area to contact the patient's body. Straps 113 may each be permanently secured at one end 121 to the top surface 120 of one lobe 114 and can be removably secured at the other end 122 to a diametrically opposite lobe 114 by a suitable releasable fastener. As hereinabove discussed, a suitable fastener may be a hook and loop fastener. A loop pad 123 may be secured to top surface 120 of lobe 114 and a corresponding loop pad 124 is secured to end 122 of a respective strap 113.

The circular configuration of the retention apparatus 110, with radial lobes 114, has been found to be quite suitable for application to various contours on the patient's body, such as the shoulder, knee, elbow or coccyx region. As such, the retention apparatus 110 is well suited for decubiti, lesions or similar wounds.

Figure 5:
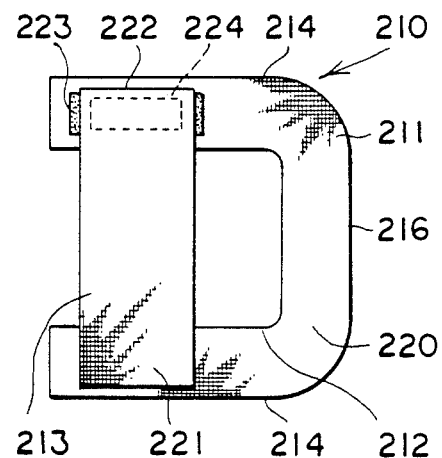
FIG. 5 is another alternative configuration for a surgical wound dressing retention apparatus embodying the concept of the present invention.

While the foregoing discussion is directed to embodiments of a retention apparatus having frameworks which totally encircle the wound, it is recognized that such is not a necessity of the present invention. The foregoing advantages and characteristics have been found to be associated with at least one alternative embodiment wherein the framework does not fully encircle the wound. With reference to FIG. 5, such an alternative embodiment of a surgical wound dressing retention apparatus is indicated generally by the numberal 210.

The surgical wound dressing retention apparatus 210 employs a substantially C-shape framework 211. Such a framework 211 is suitable for use in conjunction with wounds to the eye, wherein the bridge of the nose would otherwise constitute an obstacle for other framework shapes.

An opening 212, through which suitable wound dressing may be applied, is bounded on three sides by oppositely positioned retention legs 214 and end leg 216. At least one flexible strap 213 bridges opening 212 between retention legs 214. Strap 213 may be permanently secured at one end 221 to top surface 220 of one retention leg 214 and can be removably secured at the opposite end 222 to the other retention leg 214 by a suitable releasable fastener. If a hook and loop fastener is employed, a loop strip 223 may be secured to retention leg 214 while a corresponding hook pad 224 is carried by end 222 of strap 213.

Particularly if retention apparatus 210 is used in conjunction with wounds to the eye, it may be more desirable to have both ends 221 and 222 of strap 213 secured with releasable fasteners. Strap 213 can then be completely removed from framework 211 to permit unobstructed examination and treatment of the eye.

In each of the foregoing embodiments, it should be appreciated that one or more straps may be employed to facilitate retention of the wound dressing within the opening and on the wound. It should also be appreciated that, with the straps fastened in place, portions of the wound dressing and the opening remain accessible. This permits limited access to the wound itself for the routing of irrigation and/or drainage tubes, intravenous lines, catheters, electrical leads and the like. Similarly, limited access is provided for surgical supports and restraints, (as, for example, the type used for maintaining the position of bones and implants) during the recovery stage.

When flexible tubes or leads are employed, it is necessary to restrain the same so as not to be pulled accidentally from the wound opening. In the past this normally required the tube or lead to be taped to the patient's body in the vicinity of the wound. However, as the tape may require changing whenever the wound is attended to, it soon becomes evident that such tape will, itself, aggravate the wound and the surrounding skin.

Figure 6:
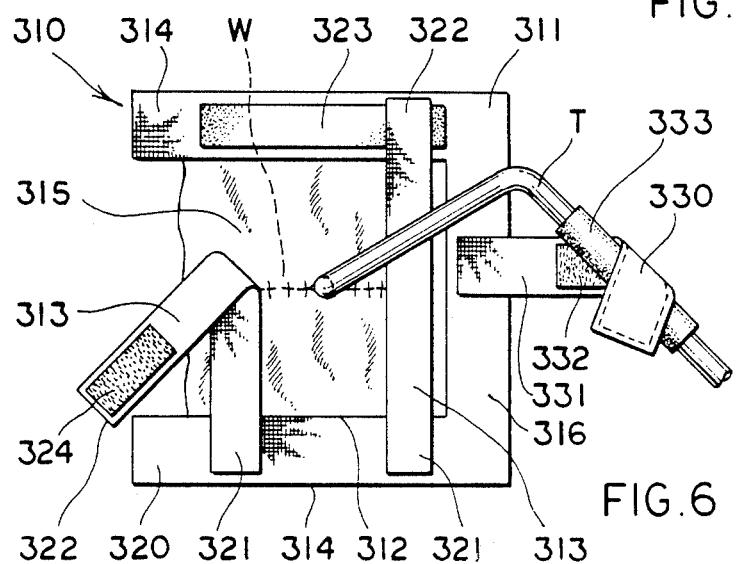
FIG. 6 is still another alternative configuration for a surgical wound dressing retention apparatus embodying the concept of the present invention.

Another embodiment of the present invention, having the advantages and characteristics heretofore described, addresses the need to provide suitable restraint for tubes and leads. Such an alternative embodiment of a surgical wound dressing retention apparatus is indicated generally by the numeral 310 in FIG. 6 of the attached drawings. As with the surgical wound dressing retention apparatus 210 described hereinabove, this alternative embodiment of retention apparatus 310 employs a substantially C-shape framework 311. Such a framework 311 enables retention apparatus 310 to be positioned about the wound W after a tubing T, or the like, has been positioned within the wound opening. Of course, depending on the nature of the article extending from the wound W, framework 311 may completely encircle the wound W or it may even possess a slit in one leg thereof to facilitate positioning around the tube T.

An opening 212, through which wound dressing material 315 can be applied and packed onto the wound W and around the tubing T is bounded on three sides by retention legs 314 and an end leg 316. Preferably at least a pair of straps 313 bridge opening 312, passing on opposite sides of the tubing T so as to position it therebetween.

As heretofore described, straps 313 may be permanently secured at one end 321 to top surface 320 of one retention leg 314, and can be removably secured at the opposite end 322 to top surface 320 of the other retention leg 314 by a suitable releasable fastener. A loop strap 323 of a hook and loop fastener can be secured to top surface 320 of retention leg 314 while the corresponding hook pads 324 can be carried on the ends 322 of straps 313.

Retention of tubing T, or the like, is facilitated by a flexible retention strap 330 which is secured at one end 331 to framework 311. Retention strap 330 may be removably secured to framework 311 or for ease of manufacturing it may be permanently secured thereto.

Retention strap 330 carries one half of a hook and loop fastener, preferably a hook strip 332. A corresponding sleeve 333 of loop material is secured to tubing T, or the like. When the wound W has been suitably dressed, retention strap 330 is wrapped in engagement with loop sleeve 333 so as to securely restrain the tubing T relative to framework 311, and the wound W.

It should be appreciated that while a hook and loop fastener is disclosed to restrain tubing T, other releasable fasteners, such as clips or releasable tape or the like, may likewise be employed with suitable results.

While the foregoing disclosure is directed primarily to a dressing retention apparatus usable with surgical wounds, it likewise is usable in other applications requiring the need to provide replaceable wound dressing. Accordingly, the present invention may be used, with favorable results, to secure dressing material to cuts, abrasions, burns, IV's, catheters, pressure ulcers, donor sites and other areas in need of skin protection.

Thus, in view of the foregoing disclosure, it should be evident that a surgical wound dressing retention apparatus embodying the concept of the invention disclosed herein enables the wound to be treated, and the dressing material changed, as needed with minimal trauma to the wound and the surrounding tissue and skin. Furthermore, the disclosed invention permits limited access to the wound region to accommodate tubes, leads or other instruments extending into the wound; and in the case of flexible tubes and leads, to provide suitable restraint thereto to prevent accidental extraction from the wound. As such, the foregoing invention constitutes an advantageous contribution to the art.

I claim:

1. Apparatus for retaining wound dressing to a wound on a patient's body, comprising:
   resilient frame means positionable proximate to the wound, said frame means having a body engaging surface for selective engagement with the patient's body and a top surface opposite said body engaging surface, said frame means presenting a dressing receiving region continually accessible from said top surface when said body engaging surface is engaged with the patient's body;
   means for retaining the wound dressing, said means for retaining bridging a portion of said dressing receiving region; and
   means for removably securing said means for retaining to a portion of said frame means.

2. Apparatus for retaining wound dressing according to claim 1 wherein said frame means substantially encircles said dressing receiving region.

3. Apparatus for retaining wound dressing according to claim 2 wherein said frame means is a continuous member.

4. Apparatus for retaining wound dressing according to claim 1 wherein said frame means partially encircles said dressing receiving region.

5. Apparatus for retaining wound dressing according to claim 4 wherein said frame means is C-shaped.

6. Apparatus for retaining wound dressing according to claim 1 wherein said means for retaining the wound dressing includes at least one flexible strap.

7. Apparatus for retaining wound dressing according to claim 6 wherein said frame means includes a first region positioned on one side of said dressing receiving region and at least a second region positioned on another side of said dressing receiving region; at least one said flexible strap bridging said dressing receiving region from said first region to said second region of said frame means.

8. Apparatus for retaining wound dressing according to claim 7 wherein said first region and said region of said frame means are positioned on opposite sides of said dressing receiving region.

9. Apparatus for retaining wound dressing according to claim 7 wherein said means for removably securing includes a releasable fastener operatively associated with at least one end of said flexible strap and a corresponding said region of said frame means.

10. Apparatus for retaining wound dressing according to claim 9 wherein said releasable fastener is a hook and loop fastener.

11. Apparatus for retaining wound dressing according to claim 1 further comprising means for holding an article in relationship to said frame means.

12. Apparatus for retaining wound dressing according to claim 11 wherein said means for holding includes a flexible strap secured to said frame means and a releasable fastener operatively associated with said flexible strap.

13. Apparatus for retaining wound dressing according to claim 12 wherein said releasable fastener is a hook and loop fastener.

14. Apparatus for retaining wound dressing according to claim 1 further comprising means for securing said frame mean proximate to the wound.

15. Apparatus for retaining wound dressing according to claim 14 wherein said means for securing includes adhesive carried on said body engaging surface.

* * * * *

UNITED STATES PATENT AND TRADEMARK OFFICE
CERTIFICATE OF CORRECTION

PATENT NO. : 4,732,146
DATED : March 22, 1988
INVENTOR(S) : Ronald J. Fasline, D.O. and Randall J. Hartwig, D.O.

It is certified that error appears in the above-identified patent and that said Letters Patent are hereby corrected as shown below:

Col. 1, line 16, after "skin" insert --or--.

Col. 1, line 25 & line 42, delete the word "agravate" and substitute therefor the word --aggravate--.

Col. 1, line 62, delete the word "tubs" and substitute therefor --tubes--.

Col. 3, line 26, after "straps" delete the numeral "15" and substitute therefor --13--.

Col. 3, line 65, delete the word "cirteria" and substitute therefor --criteria--.

Col. 4, line 38, delete the word "staps" and substitute therefor --straps--.

Col. 6, line 27, delete the numeral "212" and substitute therefor --312--.

Signed and Sealed this

Ninth Day of August, 1988

*Attest:*

*Attesting Officer*

DONALD J. QUIGG

*Commissioner of Patents and Trademarks*